United States Patent [19]

Dudar et al.

[11] Patent Number: 5,195,992
[45] Date of Patent: Mar. 23, 1993

[54] PROTECTOR SHIELD FOR NEEDLES

[75] Inventors: Thomas E. Dudar, Palatine; Vincent C. Desecki, Ingleside, both of Ill.

[73] Assignee: Baxter International Inc., Deerfield, Ill.

[21] Appl. No.: 193,457

[22] Filed: May 13, 1988

[51] Int. Cl.⁵ ............................................. A61M 25/00
[52] U.S. Cl. ...................................... 604/283; 604/905; 604/192; 604/411; 285/361
[58] Field of Search .................. 604/192, 110, 86, 160, 604/263, 283, 197, 198, 194, 806, 284, 191, 905, 413, 411, 51; 285/361, 396, 402

[56] References Cited

U.S. PATENT DOCUMENTS

| | | | |
|---|---|---|---|
| 2,230,098 | 1/1941 | Wurzburger | 285/361 |
| 3,648,684 | 3/1972 | Barnwell et al. | |
| 3,974,832 | 8/1976 | Kruck | 604/205 X |
| 3,976,073 | 8/1976 | Quick et al. | |
| 3,986,508 | 10/1976 | Barrington | 604/905 |
| 3,993,063 | 11/1976 | Larrabee | |
| 4,019,512 | 4/1977 | Tenczar | 604/905 |
| 4,076,285 | 2/1978 | Martinez | |
| 4,116,196 | 9/1978 | Kaplan et al. | |
| 4,161,949 | 7/1979 | Thanawalla | |
| 4,232,669 | 11/1980 | Nitshke | 604/192 |
| 4,392,499 | 7/1983 | Towse | 128/764 |
| 4,411,662 | 10/1983 | Pearson | |
| 4,432,759 | 2/1984 | Gross et al. | |
| 4,432,765 | 2/1984 | Oscarsson | |
| 4,508,367 | 4/1985 | Oreopoulos et al. | |
| 4,511,359 | 4/1985 | Vaillancourt | 604/411 |
| 4,752,292 | 6/1988 | Lopez et al. | 604/244 |
| 4,767,412 | 8/1988 | Hymanson | |
| 4,784,650 | 11/1988 | Coburn | 604/272 |
| 4,834,716 | 5/1989 | Ogle | 604/192 |
| 4,878,897 | 11/1989 | Katzin | 604/86 |
| 4,880,414 | 11/1989 | Whipple | 604/283 |
| 4,889,527 | 12/1989 | Herrli | 604/29 |
| 4,932,944 | 6/1990 | Jagger et al. | 604/191 |
| 4,946,495 | 8/1990 | Lynn et al. | 604/192 |
| 4,964,855 | 10/1990 | Todd et al. | 604/283 |
| 4,981,469 | 1/1991 | Whitehouse et al. | 604/86 |

FOREIGN PATENT DOCUMENTS

| | | |
|---|---|---|
| 1105959 | 7/1981 | Canada ........................ 604/905 |
| 114677 | 8/1984 | European Pat. Off. |
| 240987 | 10/1987 | European Pat. Off. |
| 2364655 | 4/1978 | France |
| 863416 | 6/1986 | PCT Int'l Appl. |

*Primary Examiner*—C. Fred Rosenbaum
*Assistant Examiner*—Mark O. Polutta
*Attorney, Agent, or Firm*—Amy L. H. Rockwell; Paul C. Flattery; Paul E. Schaafsma

[57] ABSTRACT

A protector shield is provided for a needle to protect from injury to the hand and touch contamination of the needle. The protector shield comprises an arcuate wall, longitudinally positionable about the pointed end of a tubular needle in spaced relation to it. The arcuate wall defines an open side, and an arcuate arm extends from the arcuate wall across a portion of the open side. The arm extends generally circumferentially about the needle so that the protector shield may be used to lock the needle into engagement with a Y-type injection site.

26 Claims, 1 Drawing Sheet

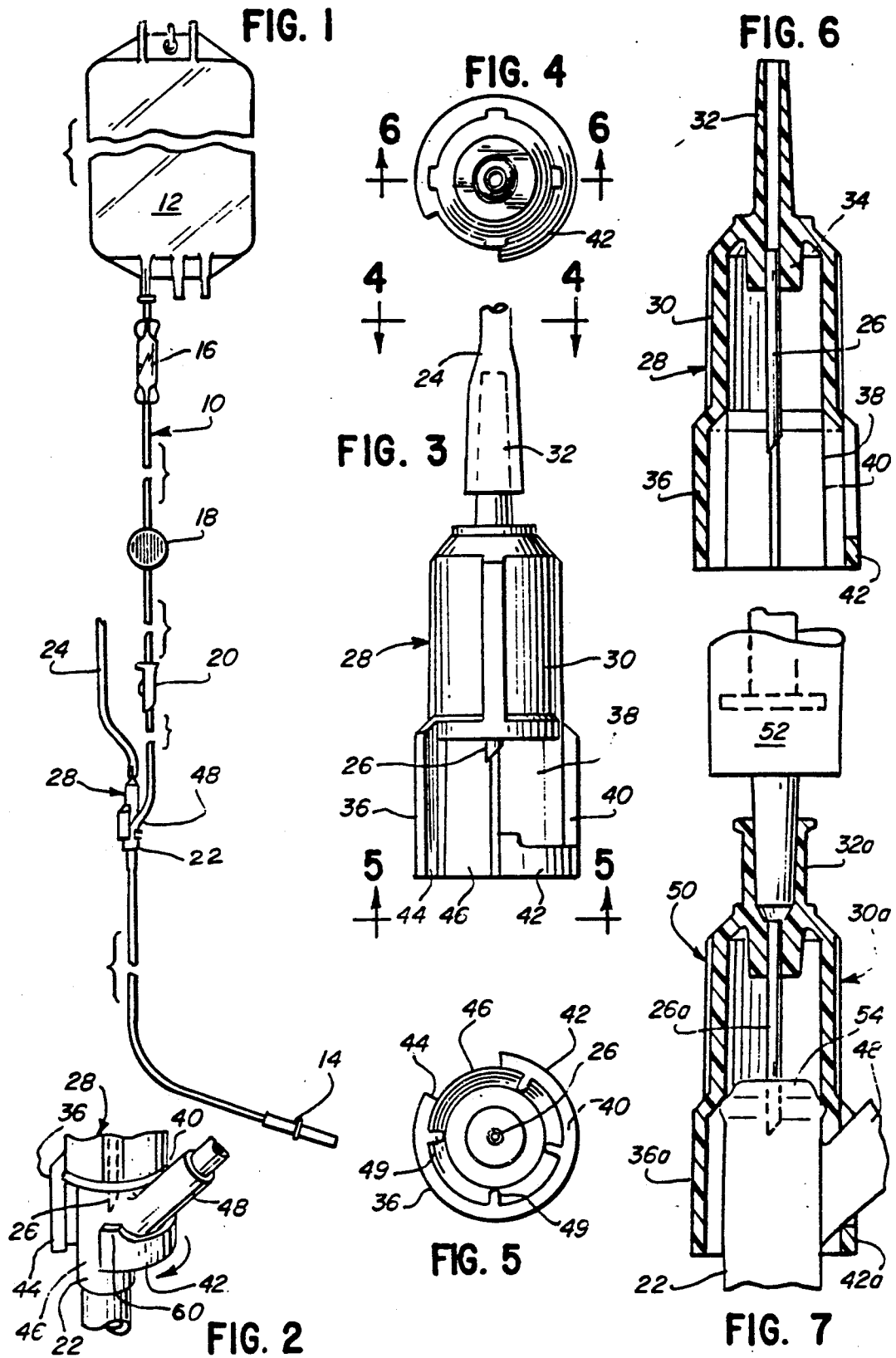

PROTECTOR SHIELD FOR NEEDLES

TECHNICAL FIELD

Tubular protectors for medical needles are well known in the prior art. For example, in Barnwall et al. U.S. Pat. No. 3,648,684, a shielded needle is shown in penetrating relation with the rubber septum of a container mouth. In Larrabee U.S. Pat. No. 3,993,063, a more complex protective shielding assembly is disclosed. Thanawalla U.S. Pat. No. 4,161,949 discloses an aseptic system having a plurality of tubular shields, while Nitshke U.S. Pat. No. 4,232,669 discloses a protective sheath for a syringe needle.

The above cited references are only a few of the designs of protective needle sheaths that are available to the prior art, being set forth for illustrative purposes.

It is of course desirable to provide a sheath needle for a blood set, or an enteral or parental solution set in which the needle is protected from touch, both to prevent needle sticks to the hand, and also to prevent touch contamination of the needle. At the same time, it is necessary for the needle to be able to make desired penetrations of access sites so that aseptic connections may be made for the administration of supplementary drugs, blood components or, the like, or for the taking of desired samples. Also, it would be desirable for the needle to be secured into locked relationship with the appropriate connection site, in those circumstances where a connection of substantial duration is desired, as in the instance where supplemental medication is to be added to a Y site in a conventional parenteral solution set. If the needle could be easily locked into its connected relation with an injection site, the chances of accidental dislodgement of the needle connection would of course be significantly reduced.

By the invention of this application a protector shield for a needle is provided in which the chances of touch contamination of the needle or injury from the needle may be substantially eliminated, but the needle is still capable of making connections with appropriate needle access sites in a medical solution delivery set or the like for blood or other medical solutions. Additionally, the protector shield of this invention is capable of locking into connected relation with certain needle access sites, for example a Y-type needle access site of a type typically positioned in a parenteral solution set between the ends thereof, for not only protecting against touching of the needle with the fingers or the hands, but also to provide the desired locking action which can prevent accidental separation of the needle from its access site until that action is desired.

DESCRIPTION OF THE INVENTION

This invention pertains to a protector shield for a needle which comprises an arcuate wall, longitudinally positionable about the pointed end of a tubular needle in spaced relation thereto. Typically, the needle is in substantially coaxial relation with the axis of the arcuate wall, which is in circumferential, essentially surrounding relation with the longitudinally extending needle.

The arcuate wall defines an open side, with an arcuate arm extending from the arcuate wall across a portion of the open side, leaving a circumferential space across the open side which the arm does not traverse. The arm extends generally circumferentially about the needle. The protector shield may be used to lock the needle into engagement with a Y-type injection site or other appropriately designed site by means of the circumferentially extending arm rotating underneath the projecting Y arm of the injection site, or any other appropriate projection of any injection site.

Hence, one may connect a needle, protected by the protector shield of this invention, by pressing it through an injection site. One then rotates the protector shield to cause the arm to rotate into engagement with a side projection of the injection site for locking the two parts into connected relation, until it is desired to separate them.

The protector shield of this invention may be a separate part, attachable to a needle in a conventional manner. However, in the specific embodiments of this invention, the needle and protector shield are manufactured as a single, connected piece. The protector shield may be insert molded about the needle, with the point of the needle being spaced therefrom.

Preferably, the pointed needle end is in recessed relation with the forward end of the arcuate wall. Also, the arcuate arm which is used to lock the shield in position on a Y-type injection site or the like is preferably positioned forward of the needle end.

The arcuate wall of the protector shield of this invention preferably defines an arc about the needle of essentially 150 to 240 degrees. Accordingly, although the shielding is not perfect, it is very difficult to bring one's finger into contact with a properly designed protector shield in accordance with this invention, particularly in view of the fact that the arcuate arm provides additional protection of the needle, despite the side aperture.

The arcuate wall preferably defines a rearward end, and the wall is attached at its rearward end to a forward end of a tubular member which may be used as a base or housing to hold the needle. The tubular member may also carry a connector member for connection of the protector shield with tubing of a set, a hypodermic needle syringe, or the like.

Thus, various medical apparatus such as administration sets or syringes may be equipped with needles protected with the shield of this invention, for protection against injury and touch contamination, and also for a locking of the needle in place on appropriate injection sites.

DESCRIPTION OF THE DRAWINGS

In the drawings, FIG. 1 is a plan view of a conventional parenteral solution administration set, having an intermediate Y-type injection site into which an injection needle from another set penetrates, being locked in position by the protector shield of this invention;

FIG. 2 is a fragmentary perspective view of a portion of FIG. 1, showing part of the protector shield of this invention and its locking relationship;

FIG. 3 is an enlarged elevational view of the protector shield of FIGS. 1 and 2;

FIG. 4 is a view of the locking shield of FIG. 3 taken along line 4—4 thereof;

FIG. 5 is a view of the protector shield of FIG. 3 taken along line 5—5 thereof;

FIG. 6 is a longitudinal sectional view of the protector shield of FIG. 3; and

FIG. 7 is a longitudinal sectional view of an alternate embodiment of the protector shield of this invention, shown in locked relation with a Y site on a set and connected to a syringe for adminstration of supplemental medication.

DESCRIPTION OF SPECIFIC EMBODIMENTS

Referring to FIG. 1, a conventional parenteral solution administration set 10 is shown, being connected to a flexible container 12 of parenteral solution at one end, and carrying at its other end a shielded intravenous needle 14, for connection with the venous system of a patient to deliver the parenteral solution of container 12 to the patient. As is conventional, a drip chamber 16, a hydrophobic vent 18, a flow control clamp 20, and a Y-type injection site 22 are provided to set 10.

The forward end of a conventional supplemental medication set 24 is shown to be in connection with Y-type injection site 22 of set 10, typically for the purpose of providing supplemental medications such as antibiotics and the like to the patient without the need of making another intravenous connection.

Referring also to FIGS. 2 through 6, set 24 carries about its connection needle 26 a protector shield 28 of this invention. Protector shield 28 comprises a tubular portion 30 which carries at its rear end a tubular extension 32, which may fit in sealing, connected relation into the bore of the tubing of set 24. Needle 26, as shown in FIG. 6, may be permanently carried in molded, inner tubular member 34 as the result of an insert molding process, or by any other desired manufacturing technique. Tubular portion 30 of protector shield 28 carries at its forward end an arcuate wall 36, which defines an open side 38. Arcuate wall extends in a generally circumferential relation about needle 26, with the needle 26 being on the axis of arcuate wall 36 and thus spaced within the wall. From one side edge 40 of arcuate wall 36, an arcuate arm 42 extends across a portion of open side 38 as shown, but spaced from the other side 44 of arcuate wall 36, so that a gap 46 is provided to permit the entry of side arm 48 of Y-type injection site through gap 46 as needle 26 is advanced into the rubber septum of the injection site. Arcuate wall 36 defines an arc about needle 26 of approximately 180°-200°, from side 40 needle to side 44, to provide substantial shielding to needle 26, the outer end of which is in generally recessed relation to wall 36, as shown particularly in FIG. 6.

Accordingly, as one connects needle 26 to the Y-type injection site 22, arm 48 of the injection site can slide through space 46. The alignment of the rubber septum which is conventionally on top of injection site 22 may be controlled by the presence of longitudinal internal ribs 49, which can serve as guides to assure that needle 26 provides proper, central penetration of the conventional top septum of the Y-type injection site.

After side arm 48 has passed through space 46, as shown in FIG. 2, one may rotate protector shield 28 to bring arm 42 under side arm 48 to prevent the accidental withdrawal of needle 26 from the injection site. Enlarged end 60 of arm 42 reduces the chance that the system may accidentally rotate into unlocked relationship again, until it is deliberately desired to unlock the system and separate Y site 22 from needle 26.

Thus, the protector shield of this invention provides good protection against touching of or injury by needle 26, while at the same time it provides the means where needle 26 may be locked into engaged relation with an injection site such as Y site 22.

It will be noted that arcuate wall 36 defines the section of a cylinder having a diameter which is larger than that of tubular portion 30. The use of this sort of a double-diameter configuration facilitates the manufacturing of the specific embodiment shown in that one can use straight-draw molding without side action for its manufacture due to the differing diameters of the two sections 30 and 36.

Turning now to FIG. 7, a second embodiment of the protector shield of this invention is disclosed, the structure and function thereof being identical to that of the first embodiment except as otherwise described herein.

As before, protector shield 50 defines a tubular portion 30a which carries needle 26a having a spaced, downwardly projecting free end. Tubular portion 30a also carries arcuate wall 36a, of similar design to arcuate wall 36. As before, arcuate wall 36a carries arcuate arm 42a for purposes of grasping side arm 48 of a Y-type injection site 22.

Protector shield 50 may, in fact, be of identical design to protector shield 28, with the exception that rear fitting 32a is in the form of a tapered luer connector, to permit connection with a conventional syringe 52. Thus, syringe 52 may be filed with the desired drug or other material for injection into Y-site 22. It is connected to the protector shield 50 of this invention. The shield is applied to Y-site 22, with needle 26a penetrating rubber septum 54 on top of Y-site 22, to permit expulsion of the contents of syringe 52 into Y-site 22 and thus down the set to which it is attached, to the patient or other destination.

The above has been offered for illustrative purposes only, and is not intended to limit the scope of the invention of this application, which is defined in the claims below.

That which is claimed is:

1. A protector shield for a needle, which comprises an arcuate wall, longitudinally positionable about the pointed end of a tubular needle in spaced relation thereto, said arcuate wall defining an open side, and an arcuate arm extending from said arcuate wall across a portion of said open side, said arm extending generally circumferentially about said needle, whereby said protector shield may be used to lock said needle into engagement with a Y-type injection site, whereby said protector shield lockingly engages and disengages with a Y-type injection site having a side arm and septum, by rotating said arcuate arm under said side arm after insertion of said needle into said septum.

2. The protector shield of claim 1 which carries a needle in generally axial relation therewith.

3. The protector shield of claim 2 in which said pointed needle end is in recessed relation with the forward end of said arcuate wall.

4. The protector shield of claim 2 in which said arcuate arm is positioned forward of said needle end.

5. The protector shield of claim 2 in which said arcuate wall defines an arc about said needle of essentially 150 to 240 degrees.

6. The protector shield of claim 2 in which said arcuate wall defines a rearward end, said wall being attached at said rearward end to a forward end of a tubular member.

7. The protector shield of claim 6 in which the diameter of said arcuate wall is greater than the diameter of said tubular member, to facilitate molding thereof.

8. The protector shield of claim 2 in which said arcuate wall carries a plurality of inwardly projecting, longitudinally extending guide ribs.

9. The protector shield of claim 2 which defines a rearward luer fitting which communicates with said tubular needle, for connection with an injection syringe or the like.

10. The protector shield of claim 2 which defines a rearward fitting which communicates with said tubular needle, for connection with flexible tubing of a medical administration set.

11. A protector shield for a needle, which comprises an arcuate wall, longitudinally positionable about the pointed end of a tubular needle in spaced relation and positioned in generally axial relation thereto, said pointed end of the needle being in recessed relation with the forward end of said arcuate wall, said arcuate wall defining an open side, and an arcuate arm extending from said arcuate wall across a portion of said open side, said arm being positioned forward of said needle end, and extending generally circumferentially about said needle, whereby said protector shield may be used to lock said needle into engagement with a Y-type injection site, whereby said protector shield lockingly engages and disengages with a Y-type injection site having a side arm and septum, by rotating said arcuate arm under said side arm after insertion of said needle into said septum.

12. The protector shield of claim 11 in which said arcuate wall defines a rearward end, said wall being attached at said rearward end to a forward end of a tubular member.

13. The protector shield of claim 12 in which the diameter of said arcuate wall is greater than the diameter of said tubular member, to facilitate molding thereof.

14. The protector shield of claim 12 in which said arcuate wall caries a plurality of inwardly projecting, longitudinally extending guide ribs.

15. The protector shield of claim 12 in which said arcuate wall defines an arc about said needle of essentially 150 to 240 degrees.

16. The protector shield of claim 12 which defines a rearward luer fitting which communicates with said tubular needle, for connection with an injection syringe or the like.

17. The protector shield of claim 12 which defines a rearward fitting which communicates with said tubular needle, for connection with flexible tubbing of a medical administration set.

18. A protector shield for a needle, which comprises an arcuate wall, longitudinally positionable about the pointed end of a tubular needle in spaced relation thereto, said pointed needle end being in recessed relation with the forward end of said arcuate wall, said needle being positioned in generally axial relation with said arcuate wall, the arcuate wall defining an open side, and an arcuate arm positioned forward of the needle end, extending from said arcuate wall across a portion of said open side, said arm extending generally circumferentially about said needle, said arcuate wall defining a rearward end, said wall being attached at said rearward end to a forward end of a tubular member, the diameter of said arcuate wall being greater than the diameter of said tubular member, said arcuate wall defining an arc about said needle of essentially 150 to 240 degrees, whereby said protector shield lockingly engages and disengages said needle with a Y-type injection site having a side arm and septum, by rotating said arcuate arm under said arm after insertion of said needle into said septum.

19. The protector shield of claim 18 in which the inner surface of said arcuate wall defines a plurality of longitudinally positioned guide ribs.

20. The protector shield of claim 19 which defines a rearward luer fitting which communicates with said tubular needle, for connection with an injection syringe or the like.

21. The protector shield of claim 20 which defines a rearward tubular fitting which communicates with said tubular needle for connection with flexible tubing of a medical administration set.

22. A connector assembly for joining a Y-tube and a fluid connector, the Y-tube including an attached sidearm, the assembly comprising:
  a. a resilient, molded, tubular body providing an elongated sidewall and distal and proximal ports, the fluid connector being connected to the distal port, and to an I.V. source, syringe, and the like, and the Y-tube being lockingly connectable to the tubular body adjacent its proximal port;
  b. a recessed needle mounted within the distal port of the tubular body in liquid connection with the fluid connector; and
  c. a cut-out area defined on the sidewall, and extending from the proximal port of the tubular body, the cut-out area including i. an alignment portion along which the tubular body slides as it deformably fits along the Y-tube and engages therewith, and ii. a notch area defined by the cut-out area; whereby, the tubular body and Y-tube are locked together by sliding the Y-tube along the alignment portion, and deforming the sidearm of the Y-tube into the notch area.

23. A connector assembly for joining a Y-tube and a fluid connector, the Y-tube including an attached sidearm, the assembly comprising:
  a. a resilient, tubular body providing an elongated sidewall and distal and proximal ports, the fluid connector being connected to the distal port, and the Y-tube being lockingly connectable to the tubular body adjacent its proximal port;
  b. a recessed needle mounted within the distal port of the tubular body in liquid connection with the fluid connector; and
  c. a cut-out area defined on the sidewall, and extending from the proximal port of the tubular body, the cut-out area including i. an alignment portion along which the Y-tube slides as it moves upwardly along the cut-out area of the sidewall, and ii. a notch area also defined by the cut-out area; whereby, the tubular body and Y-tube are locked together by sliding the Y-tube along the alignment portion, and moving the sidearm of the Y-tube into the notch area.

24. The connector assembly of claim 23, wherein said recessed needle is disposed along the axis of said tubular body.

25. The connector assembly of claim 23, wherein resilient tubular body includes a luer fitting.

26. A connector assembly for joining a Y-tube and a fluid connector, the Y-tube including an attached sidearm, the assembly comprising:
  a. a resilient, tubular body providing an elongated sidewall and distal and proximal ports, the fluid connector being connected to the distal port, and the Y-tube being lockingly connectable to the tubular body adjacent its proximal port;
  b. a recessed needle mounted within the distal port of the tubular body in liquid connection with the fluid connector; and
  c. a cut-out area defined on the sidewall, and extending from the proximal port of the tubular body, the cut-out area including i. an alignment portion along which the Y-tube slides as it moves upwardly along the cut-out area of the sidewall, and ii. an notch area defined by the cut-ut area; whereby, the tubular body and Y-tube are locked together by sliding the Y-tube along the alignment portion, and then rotating the sidearm of the Y-tube into the notch area.

* * * * *

UNITED STATES PATENT AND TRADEMARK OFFICE
CERTIFICATE OF CORRECTION

PATENT NO.   :  5,195,992

DATED        :  March 23, 1993

INVENTOR(S)  :  Dudar et al.

It is certified that error appears in the above-identified patent and that said Letters Patent is hereby corrected as shown below:

Column 3, line 40, after "40" delete "needle"

Column 4, line 20, delete "filed" and insert --filled--

Column 4, line 25, delete "expulusion" and insert --expulsion--

Column 5, line 32, delete "caries" and insert --carries--

Column 5, line 43, delete "tubbing" and insert --tubing--

Column 7, line 3, delete "an" and insert --a--

Column 7, line 4, delete "cut-ut" and insert --cut-out--

Signed and Sealed this

Eighteenth Day of January, 1994

Attest:

BRUCE LEHMAN

*Attesting Officer*    *Commissioner of Patents and Trademarks*